United States Patent [19]

Riemenschneider

[11] Patent Number: 5,728,872

[45] Date of Patent: Mar. 17, 1998

[54] STABILIZED ACRYLIC ACID COMPOSITIONS

[76] Inventor: Lutz Riemenschneider, Am Schenkenfeld 29, 97209 Veitshochheim, Germany

[21] Appl. No.: 266,330

[22] Filed: Jun. 27, 1994

[51] Int. Cl.$^6$ ............................................. C07C 57/02
[52] U.S. Cl. .................................................. 562/598
[58] Field of Search ...................................... 562/598

[56] References Cited

U.S. PATENT DOCUMENTS

| | | | |
|---|---|---|---|
| 3,334,103 | 8/1967 | Feldman et al. | 260/290 |
| 3,372,182 | 3/1968 | Hoffman et al. | 260/465.5 |
| 3,422,144 | 1/1969 | Hoffman et al. | 260/570 |
| 3,494,930 | 2/1970 | Dupeyre et al. | 260/294.7 |
| 3,502,692 | 3/1970 | Feldman et al. | 260/326.3 |
| 3,666,795 | 5/1972 | Walters | 260/504 A |
| 3,674,651 | 7/1972 | Otsuki et al. | 203/8 |
| 3,704,235 | 11/1972 | Rassat et al. | 260/292 |
| 3,733,326 | 5/1973 | Murayama et al. | 260/290 V |
| 4,021,310 | 5/1977 | Shimizu et al. | 203/8 |
| 4,127,603 | 11/1978 | Bljumberg et al. | 562/533 |
| 4,663,480 | 5/1987 | Inskip et al. | 562/598 |
| 4,665,185 | 5/1987 | Winter et al. | 546/184 |
| 4,670,131 | 6/1987 | Ferrell | 208/48 AA |
| 5,034,156 | 7/1991 | Varwig. | |
| 5,087,752 | 2/1992 | Murray et al. | 564/298 |
| 5,130,471 | 7/1992 | Heiman et al. | 560/205 |
| 5,144,091 | 9/1992 | Martan et al. | 568/479 |
| 5,221,764 | 6/1993 | Roling | 560/205 |
| 5,254,760 | 10/1993 | Winter et al. | 585/5 |
| 5,258,138 | 11/1993 | Gatechair et al. | 252/403 |
| 5,290,888 | 3/1994 | Gatechair et al. | 526/83 |
| 5,322,960 | 6/1994 | Sakamoto et al. . | |

FOREIGN PATENT DOCUMENTS

| | | |
|---|---|---|
| 0178168 | 4/1986 | European Pat. Off. . |
| 0467848 | 1/1992 | European Pat. Off. . |
| 0467850 | 1/1992 | European Pat. Off. . |
| 0468303 | 1/1992 | European Pat. Off. . |
| 0488403 | 6/1992 | European Pat. Off. . |
| A-0620206 | 10/1994 | European Pat. Off. . |
| 86103840 | 12/1987 | Japan . |
| 1127127 | 9/1968 | United Kingdom . |
| 1199351 | 7/1970 | United Kingdom . |
| 1265419 | 3/1972 | United Kingdom . |
| 1316342 | 5/1973 | United Kingdom . |
| 1432190 | 4/1976 | United Kingdom . |
| WO-A-8910343 | 11/1989 | WIPO . |

OTHER PUBLICATIONS

Zhang Ziyi and Wei Xiuying, "High Inhibition Effect of 2, 2, 6, 6 Tetra–Methyl–4–Hydroxyl–Piperidine–Oxyl on Acrylic Acid", *Chemical Journal of Chinese Universities*, vol. 4, No. 2, pp. 244–247 (1983).

Leon B. Levy, "Inhibition of Acrylic Acid Polymerization by Phenothiazine and p–Methoxyphenol", *Journal of Polymer Science: Polymer Chemistry Edition*, vol. 23, 1505–1515 (1985).

Elmer J. Rauckman, et al., "Improved Methods for the Oxidation of Secondary Amines to Nitroxides", *Synthetic Communications*, 5(6), 409–413 (1975).

Niloo Farhad, "Acrylic Acids and Acrylic Esters", Process Economics Program Report No. 6C, (Feb. 1987), Process Economics Program, Menlo Park, California 94025.

Abstract (No. CA101(25):229711j) of "Mechanism of the Synergistic Action of Binary Mixtures of Antioxidants reacting with alkyl and peroxyl radicals" (1984).

Abstract (No. 4022846) of CN 1,052,847; Orient Chemical Factory Beijin; Jul. 10, 1991.

Abstract (No. 4011597) of CN 1,041,598; Beijing Assistant Inst.; Apr. 25, 1990.

Abstract (No. 1103840) of CN 86,103,840; Jinxi Chemical Engineering Ins.; Dec. 16, 1987.

Abstract (No. 90–159052/21) of JP 2,099,323; Mitsubishi Kasei Corp.; Apr. 11, 1990.

Abstract (No. 90–101563/14) of EP 362,119; Goodyear Tire & Rubber; Apr. 4, 1990.

Abstract (No. 81–23061D/13) of SU 749,823; AS USSR Chem. Phys.; Jul. 23, 1980.

Abstract (No. 25223R) of DT 1944 233–Q; BP Chemicals; Sep. 6, 1968.

Abstract (No. 84–094116/15) of SU 1027–150–A; Sarat Univ. Mechanic.; Oct. 21, 1981.

Abstract (No. 84–222317/36) of SU 1139–722–A; Erev Okhtinsk Plast; Apr. 12, 1983.

Abstract (No. 40675U–E) of SU 350805; Jul. 22, 1969.

Abstract (No. 63593 C/36) of SU 809,609; Urals Kirov Poly; Mar. 6, 1978.

Abstract (No. 85–084672/14) of JP 0036–501–A; Adeka–Argus Chem. KK; Aug. 10, 1983.

Abstract (No. 73074 D/40) of SU 793–996; Sarat Univ. Mech. Phy.; Dec. 26, 1978.

Abstract (No. 93.844P) of NE.67.05691; B.P. Chem. Ltd.; Apr. 26, 1966.

Abstract (No. 23061 D/13) of SU 749–823; AS USSR Chem. Phys.; Mar. 29, 1978.

Abstract (No. 24647T–AEG) of GB 1271613–R; Intercontinental Chemical Co. Ltd.; Apr. 14, 1969.

(List continued on next page.)

Primary Examiner—Paul J. Killos
Attorney, Agent, or Firm—Jenkens & Gilchrist, A.M. Arismendi, Jr.

[57] ABSTRACT

A stabilized acrylic acid composition is provided in which the polymerization of the acrylic acid is inhibited during the distillation process for purifying or separating the acrylic acid as well as during transport and storage. The compositions of the present invention comprise three components: (A) acrylic acid, (B) a stable nitroxyl radical, e.g., the nitroxyl radical 4–hydroxy–2,2,6,6–tetramethyl–1–piperidinyloxy (CAS registry number 2226-96-2) (HTEMPO), and (C) a dihetero-substituted benzene compound having at least one transferable hydrogen, e.g., a quinone derivative such as the mono-methyl-ether of hydroquinone (MEHQ). During the distillation process, transport and storage, components (B) and (C) are present in a polymerization-inhibiting amount. During the distillation process, oxygen (D) is preferably added with components (B) and (C).

12 Claims, 5 Drawing Sheets

OTHER PUBLICATIONS

Abstract (No. 73553X/39) of SU 478–838; AS USSR Chem. Phys.; Sep. 17, 1973.

Abstract (No. 84–150038/24) of SU 334–845–A; AS USSR Chem. Phys.; Jul. 22, 1970.

Abstract (No. 86–101790/16) of EP 178–168–A; Amoco Corp.; Oct. 10, 1984.

Abstract (No. 85–255151/41) of SU 1147–708–A; Sarat Univ. Mech. Phy.; Jul. 12, 1983.

Abstract (No. 61485Y/35) of DT 2706–583; AS USSR Chem. Phys.; Feb. 20, 1976.

Abstract (No. 485438/26) of SU 621–692; AS USSR Chem. Phys.; Apr. 28, 1975.

Abstract (No. 24537T–AE) of DT 2149652–Q; BP Chemicals Ltd.; Oct. 5, 1970.

Abstract (No. 24538T–AE) of DT 2149670–Q; BP Chemicals Ltd.; Oct. 5, 1970.

Abstract (No. 22451U–AE) of BE 789433–Q; BP Chemicals Ltd.; Sep. 30, 1971.

Abstract of FR 1,527,237; BP Chemical (UK) Ltd.; Apr. 26, 1966.

Abstract (No. 92–033642/05) of DE 023239; BASF AG; Jul. 21, 1990.

Abstract (No. 92–260067/32) of DE 410879–A; BASF AG; Jan. 23, 1991.

Abstract (No. 92–034085/05) of EP 468–303–A; BASF AG; Jul. 23, 1990.

Abstract (No. 89–158743/22) of DE 3837–955–A; BASF AG; Nov. 9, 1981.

Abstract (No. 64499V/37) of Be 811–571; BASF AG; Feb. 27, 1973.

Abstract (No. 00050W/01) of BE 816–394; BASF AG; Jun. 16, 1973.

Abstract (No. 79516X/43) of DT 2513–405; BASF AG; Mar. 26, 1975.

Abstract (No. 13067X/08) of BE 831–990; BASF AG; Jul. 31, 1974.

Abstract (No. 89–166489/23) of DE 3740–271–A; BASF AG; Nov. 27, 1987.

Abstract (No. 89–208386/29) of EP 324–414–A; BASF AG; Jan. 15, 1988.

Abstract (No. 91–326536/45) of DE 4013–725–A; BASF AG; Apr. 28, 1990.

Abstract (No. 85–184373/31) of DE 1793–031–A; Badische Anilin Sod; Jul. 25, 1968.

Abstract (No. 04,572Q) of BE 705,558; Badische Aniline; Oct. 25, 1966.

Abstract (No. 04,542Q) of NE 67,14661; Badische Anilin; Oct. 28, 1966.

Abstract (No. 13,319Q) of NE 68,04760; Badische Anilin; Apr. 6, 1967.

Abstract (No. 13,706Q) of BE 713,362; Badische Anilin; Apr. 8, 1967.

Abstract (No. 30,871Q) of NE 69,00466; Badische Anilin; Jan. 11, 1968.

Abstract (No. 30,296Q) of BE 726,721; Badische Anilin; Jan. 11, 1968.

Abstract (No. 39,972Q) of BE 723,877; Badische Anilin; May 11, 1968.

Abstract (No. 41,994Q) of BE 733,773; Badische Anilin; May 30, 1968.

Abstract (No. 59421R–AE) of BE 746202–Q; Badische Anilin; Feb. 22, 1969.

Abstract (No. 33781T–AE) of BE 775252–Q; Badische Anilin; Nov. 18, 1970.

Abstract (No. 32835V 18) of DT 2249–922; BASF AG; Oct. 12, 1972.

Abstract (No. 10823W/07) of BE 818–210; BASF AF; Jul. 27, 1973.

Abstract (No. 68139 C/39) of EP 15–569; BASF AG; Mar. 12, 1979.

Abstract (No. 71677 C/41) of DT 2909–67; BASF AG; Mar. 12, 1979.

Abstract (No. 83–706323/28) of DE 3151–805–A; BASF AG; Dec. 29, 1981.

Abstract (No. 83–766186/38) of EP 88–328–A; BASF AG; Mar. 10, 1982.

Abstract (No. 83–766185/38) of EP 88–327–A; BASF AG; Mar. 10, 1982.

Abstract (No. 86–157068/25) of EP 184–790–A; BASF AG; Dec. 12, 1984.

Abstract (No. 35,347Q) of NE 69,03902; Badische Anilin; Mar. 14, 1968.

Abstract (No. 22,602Q) of GE 1,518,585; Badische Anilin; Aug. 19, 1965.

Abstract (No. 49632R–AE) of DT B82908..R28; Badische Anilin; Jul. 20, 1965.

Abstract (No. 89,770P) of BE 694,209; Badische Anilin; Feb. 19, 1966.

Abstract (No. 13,277Q) of NE 68,04300; Badische Anilin; Apr. 3, 1967.

Abstract (No. 07394U–AE) of DT 136396..U06; Badische Anilin; Jul. 21, 1971.

Abstract (No. 74745T–AE) of DT 121123..T47; Badische Anilin; Apr. 29, 1971.

Abstract (No. 19402V–11) of BE 803–984; BASF AG; Aug. 24, 1972.

Abstract (No. 82956V/48) of DT 2323–328; BASF AG; May 9, 1973.

Abstract (No. 34133X/19) of DT 2449–780; BASF AG; Oct. 19, 1974.

Abstract (No. 27110Y/16) of BE 847–154; BASF AG; Oct. 11, 1975.

Abstract (No. 89–158743/22) of DE 3837–955–A; BASF AG; Nov. 9, 1988.

Abstract (No. 25223R) of DT 1944 233–Q; BP Chemicals (UK) Ltd.; Sep. 6, 1968.

Abstract (No. 85–222317/36) of SU 1139–722–A; Erev Okhtinsk Plast; Apr. 12, 1983.

Abstract (No. 40675U–E) of SU 350805..U29; Jul. 22, 1969.

Abstract (No. 63593 C/36) of SU 709–609; Urals Kirov Poly; Mar. 6, 1978.

Abstract (No. 85–084672/14) of J6 0036–501–A; Adeka–Argus Chem KK; Aug. 10, 1983.

Abstract (No. 93,844P) of NE 67,05691; B.P. Chem. Ltd.; Apr. 26, 1966.

Abstract (No. 85–255151/41) of SU 1147–708–A; Sarat Univ. Mech. Phys.; Jul. 12, 1983.

Abstract (No. 485438/26) of SU 621–692; AS USSR Chem. Physic; Apr. 28, 1975.

Abstract (No. 24537T–AE) of GB–047169..T16; BP Chemicals Ltd.; Oct. 5, 1970.

Abstract (No. 24538T–AE) of GB–047169..T16; BP Chemicals Ltd.; Oct. 5, 1970.

Abstract (No. 22461U–AE) of GB–045536..U16; BP Chemicals Ltd.; Sep. 30, 1971.

Abstract (No. 11,246Q) of FR 1,527,237; BP Chemical (UK) Ltd.; Apr. 26, 1966.

Abstract (No. 91,844P) of NE 67,05691; B.P. Chem. Ltd.; Apr. 26, 1966.

Abstract (No. 75561S–AE) of JA 023987. .S48; Sankyo Co. Ltd.; Mar. 20, 1970.

Abstract (No. 92–026649/04) of EP 467–848–A; Ciba Geigy AG; Jul. 20, 1990.

Abstract (No. 88–354365/50) of CN 8603–840–A; Jinxi Chem. Eng. Inst.; Jun. 5, 1986.

Abstract (No. (92–026649/04) of CA 2,047,393–AA.

Abstract (No. 92,124029/16) of CN 1052–847–A; Orient Chem. Factory; Apr. 15, 1989.

C.A. 101:229711 1984.

STABILIZED ACRYLIC ACID COMPOSITIONS

FIELD OF THE INVENTION

This invention relates to acrylic acid compositions which are stabilized against the premature polymerization of the acrylic acid. More specifically, the present invention relates to stabilized acrylic acid compositions in which polymerization of the acrylic acid is inhibited during the distillation process for purifying or separating the acrylic acid as well as during transport and storage.

BACKGROUND OF THE INVENTION

Acrylic acid can be polymerized under controlled conditions to give useful polymers. In preparing acrylic acid or preparing acrylic esters from acrylic acid by either the esterification reaction or the transesterification reaction, a distillation operation for separating, concentrating or purifying is typically employed. Acrylic acid is one of the most reactive of the common vinyl monomers. It has a pronounced tendency toward oligomeric peroxide formation and toward thermal polymerization, which is accelerated by the template effect of solid polymer. Acrylic acid is different from other vinyl monomers because of the powerful electron-withdrawing properties of the carboxyl group and the ordering of monomer molecules through hydrogen bonding which facilitates polymerization under certain conditions. (See Leon B. Levy, "Inhibition of Acrylic Acid Polymerization by Phenothiazine and p-Methoxyphenol," Journal of Polymer Science: Polymer Chemistry Ed., Vol. 23, pp. 1505–1515 (1985).) It is known that the high polymerization tendency of acrylic acid becomes extremely high at elevated temperatures such as in the distillation step. Therefore, in the preparation of acrylic acid and its esters on a commercial scale, the prevention of polymerization of acrylic acid during the distillation step is extremely important to the stable operation of the process.

When distilling acrylic acid or its esters in the separation, concentration or purification step, it is known that a polymer may be formed at various places, for example, on the reverse side of the trays, the inside of the bubble caps, the external surface of the downcomers and the recessed portions on the column wall which are not perpetually wetted with a liquid containing polymerization inhibitors, as well as the hardware (e.g., bolts, nuts), the packing and the gaskets for setting up the trays at which liquid tends to stagnate. The polymers thus formed do not readily dissolve in water, acrylic acid, acrylic esters or other organic solvents. Further, once the polymer forms inside the column, it becomes a nucleus of polymerization to cause a gradual accumulation of polymer which can block the inside of the column and render impossible the continuous distillation operation. Moreover, great difficulty is involved in removing this accumulated polymer.

Previously, as a measure to inhibit the polymerization of acrylic acid or esters thereof during their distillation, there was proposed in the specification of the German Laid-Open Pat No. 2,027,655 a distillation column of a construction in which the reverse side of the trays and the inside wall of the column have been made readily wettable. Aside from this proposal, the method most widely used heretofore for inhibiting the polymerization of these compounds is that of adding a polymerization inhibitor to the distillation column.

Typical polymerization inhibitors are phenolic compounds, amine compounds, nitro compounds, quinone compounds and certain inorganic salts, e.g., CDDC. The use of stable nitroxyl radicals including those derived from hindered amine moieties has also been disclosed. Typical references are cited below.

Japanese Sho 60-36501 describes the use of hindered amines and their 1-oxyl and 1-alkyl derivatives as vinyl polymerization inhibitors to improve storage stability of monomers such as acrylate and methacrylate esters.

European Patent Application No. 178,168 A2 discloses the use of 1-oxyl substituted hindered amine compounds as stabilizers for inhibiting the polymerization of α,β-ethylenically unsaturated monocarboxylic acids during its recovery by distillation. Though acrylic acid is mentioned, only methacrylic acid is exemplified. Further, its is acknowledged therein that of the α,β-ethylenically unsaturated compounds, acrylic acid has one of the greatest tendencies to polymerize, and that it is extremely difficult to handle at elevated temperatures. This application was limited to the use of 2,2,6,6-tetramethyl-4-oxopiperidine-1-oxyl to stabilize methacrylic acid. This material was compared to 2,2,6,6-tetramethyl-piperidine-1-oxyl (i.e., without the 4-oxo) and preferred thereover. (See EP 178, 168 B1.)

GB 1,265,419 to Christopher John Brown, et al., discloses a method for minimizing polymerization of acrylic acid during distillation thereof which comprises distilling the acrylic acid in the presence of nitric oxide in the gas phase and phenothiazine in the liquid phase.

GB 1,127,127 to Hubert Charles Bailey describes the use of 1-oxyl substituted hindered amine compounds termed nitroxides therein as stabilizers for inhibiting the polymerization of acrylic acid. The nitroxide has the essential skeletal structure:

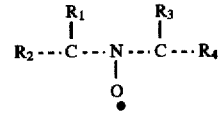

wherein $R_1$, $R_2$, $R_3$ arid $R_4$ are alkyl groups and no hydrogen is bound to the remaining valencies on the carbon atoms bound to nitrogen. The nitroxide is effective in the presence or absence of oxygen. However, in the presence of oxygen, peroxy compounds of acrylic acid tend to be formed, which on decomposition lead to the consumption of nitroxide. The nitroxides HTEMPO and di-tert-butyl nitroxide were exemplified. Comparative examples utilized BQ, HQ, PTZ, α,α'-diphenyl-β-picrylhydrazil (DPPH) or cupric chloride.

GB 1,432,190 discloses that PTZ is useful as a stabilizer during distillation of acrylic acid.

U.S. Pat. No. 5,290,888 to Gatechair, et al., discloses the use of 1-hydroxy substituted hindered amine compounds as preferred over their 1-oxyl counter-parts as effective inhibitors to prevent the premature polymerization of monomers, including acrylic acid and methacrylic acid, in either the vapor or liquid phase. The relative effectiveness of 1,4-dihydroxy-2,2,6,6-tetramethylpiperidine and 1-oxyl-4-hydroxy-2,2,6,6-tetramethylpiperidine (HTEMPO) were compared using methyl methacrylate monomer. A combination of N,N-dialkylhydroxylamines and monomethyl ether of hydroquininone (MEHQ) were effective in inhibiting the polymerization of methyl methacrylate monomer. In comparative examples, the following inhibitors alone failed to inhibit the polymerization of acrylic acid: phenothiazine (PTZ); N,N-diethylhydroxylamine (DEHA); 1-hydroxy 2,2, 6,6-tetramethylpiperidin-4-yl benzoate; 1-hydroxy-2,2,6,6-tetramethylpiperidin-4-one; and bis(1-hydroxy-2,2,6,6-tetramethylpiperidin-4-yl)sebacate.

U.S. Pat. No. 5,258,138 to Gatechair, et al., discloses the use of a hindered amine plus PTZ (or other related heterocyclic moiety) as inhibitors to prevent the premature polymerization of monomers, including acrylic acid, in either the liquid or vapor phase. Though other PTZ-related heterocyclic moieties are disclosed, only PTZ is demonstrated and claimed. Further, though the N-hydroxy substituted hindered amines are used in conjunction with PTZ, the corresponding stable nitroxyls are not used.

Z. Ziyi et al., "High Inhibition Effect of 2,2,6,6-tetramethyl-4-hydroxyl-piperidine-oxyl on Acrylic Acid," Chemical Journal of Chinese Universities, Vol. 4, No. 2, pp. 244-247 (1983) discloses the synergistic effect of the combination HTEMPO, PTZ and benzoquinone (BQ) on the polymerization of acrylic acid. The inhibiting effects or lack thereof on the polymerization of acrylic acid of the following compounds is also disclosed: HTEMPO, PTZ, hydroquinone (HQ), tetrachlorobenzoquinone (TCBQ), BQ, 1,4-nitroquinone (NQ), and phenylquinone (PQ) alone and combinations of HTEMPO with BQ, TCBQ, NQ or PQ. Improved inhibition effects were seen when HTEMPO was mixed with BQ. The most prominent effect was seen with a combination of HTEMPO, BQ and PTZ.

Chinese patent application no. 86-1-03840 (Jinx Chemical Institute) discloses the use of a mixture of HTEMPO and p-hydroxy-phenyl methyl ether (MEHQ) to prevent the polymerization of methacrylic acid and isobutyric acid (and their esters). The synergistic effect of these two components requires the presence of oxygen. Acrylic acid is neither taught nor suggested using this particular combination. Reference is made to the foregoing work of Z. Ziyi et al., but is criticized in regards to the large quantities of retarder (i.e., HTEMPO, BQ and PTZ) required thereby.

Leon B. Levy, supra, discloses the combination of PTZ and MEHQ to inhibit the polymerization of acrylic acid. MEHQ requires the presence of oxygen to function as an inhibitor.

U.S. Pat. No. 3,674,651 to Otsuki discloses the use of a combination of diphenylamine or its derivatives and an oxygen-containing gas for inhibiting the polymerization of acrylic acid. This combination can also employ BQ and/or MEHQ.

U.S. Pat. No. 4,663,480 to Inskip, et al., discloses that manganese nitrite, i.e. $Mn(NO_2)_2$, effectively inhibits undesired polymerization, e.g., thermal polymerization, of ethylenically unsaturated monomers such as unsaturated hydrocarbons, hydrocarboxyl acids and hydrocarboxyl esters. Acrylic acid is specifically exemplified.

U.S. Pat. No. 5,221,764 to Roling discloses that the combination of a cerium source compound and an aromatic amine, e.g., a phenylenediamine, may be used to inhibit the polymerization of acrylic acid. A majority of the MEHQ originally in the acrylic acid was removed prior to testing with the inhibitor composition disclosed therein.

U.S. Pat. No. 4,021,310 discloses carrying out the distillation for separating or purifying the acrylic acid obtained by the vapor phase catalytic oxidation of propylene or acrolein or acrylic esters derived from acrylic acid, in the presence of (A) at least one compound selected from the group consisting of HQ, MEHQ, cresols, phenols, t-butyl catechol (TBC), diphenylamine, PTZ's, various other compounds described in the patent, and methylene blue; (B) at least one compound selected from the group consisting of copper dimethyldithiocarbamate, copper diethyldithiocarbamate, copper dibutyldithiocarbamate (CDDC) and copper salicylate; and (C) molecular oxygen. Some of the compounds of groups (A) and (B) are recognized therein as known polymerization inhibitors of acrylic acid or its esters and that the simultaneous use of these compounds with molecular oxygen is also known. On the other hand, the '310 patent describes the simultaneous use of the three components of groups (A), (B) and (C) in the distillation of acrylic acid or its esters to obtain a synergistic effect.

Thus as noted, acrylic acid undesirably polymerizes at various stages of its manufacture, processing, handling, storage and use. A particularly troublesome problem is equipment fouling caused by polymerization in the purification stages of acrylic acid production processes. Polymerization, such as thermal polymerization, during the purification of acrylic acid, results in the loss of acrylic acid and in loss of production efficiency because the polymer often deposits in or on equipment in contact with the acrylic acid and must be removed at frequent intervals.

As has been discussed above, a wide variety of substances have been proposed for inhibiting uncontrolled polymerization, e.g., thermal polymerization, of acrylic acid. However, the heretofore proposed substances have not been entirely satisfactory. Accordingly, there is a substantial need in the art for improved compositions in which polymerization of acrylic acid is inhibited during the distillation process for purifying or separating the acrylic monomer as well as during transport and storage.

None of the above-identified references describes or suggests that a combination of (1) a stable nitroxyl (which the prior art teaches is consumed in the presence of oxygen) or its corresponding N-hydroxy substituted compound and (2) MEHQ (which the prior art teaches requires the presence of oxygen to be effective) or other related heterocyclic moiety is or could possibly be such effective inhibitors to prevent the premature polymerization of acrylic acid (in the liquid or vapor phase) in either the presence or absence of oxygen.

SUMMARY OF THE INVENTION

A stabilized acrylic acid composition is provided in which polymerization of the acrylic acid is inhibited during the distillation process for purifying or separating the acrylic acid as well as during transport and storage. The compositions of the present invention comprise three components: (A) acrylic acid, (B) a stable nitroxyl radical, e.g., HTEMPO, or its corresponding hydroxyl amine and (C) a dihetero-substituted benzene compound having at least one transferable hydrogen, e.g., a quinone derivative such as MEHQ.

During the distillation process, transport and storage, components (B) and (C) are present in a polymerization-inhibiting amount. During the distillation process, oxygen (D) is preferably added with components (B) and (C).

Preferably, component (B) is present in an amount of from about 5.8 millimolar to about 5.8 molar parts per million (ppm), and component (C) is present in an amount of from about 8 millimolar to about 16 molar ppm. If present during distillation, component (D) is preferably present in an amount of from about 1 to about 15,000 ppm, with the ppm being based on oxygen content. Component (D) may be present or added as air or molecular oxygen.

The method of the present invention excludes any process carried out for the purpose of polymerizing acrylic acid, particularly in the presence of effective amounts of polymerization catalyst. A particular application of the present invention is to inhibit the spontaneous formation of "popcorn polymer" in distillation equipment used to separate and recover acrylic acid.

IN THE DRAWINGS

DESCRIPTION OF THE INVENTION

Figure 1:
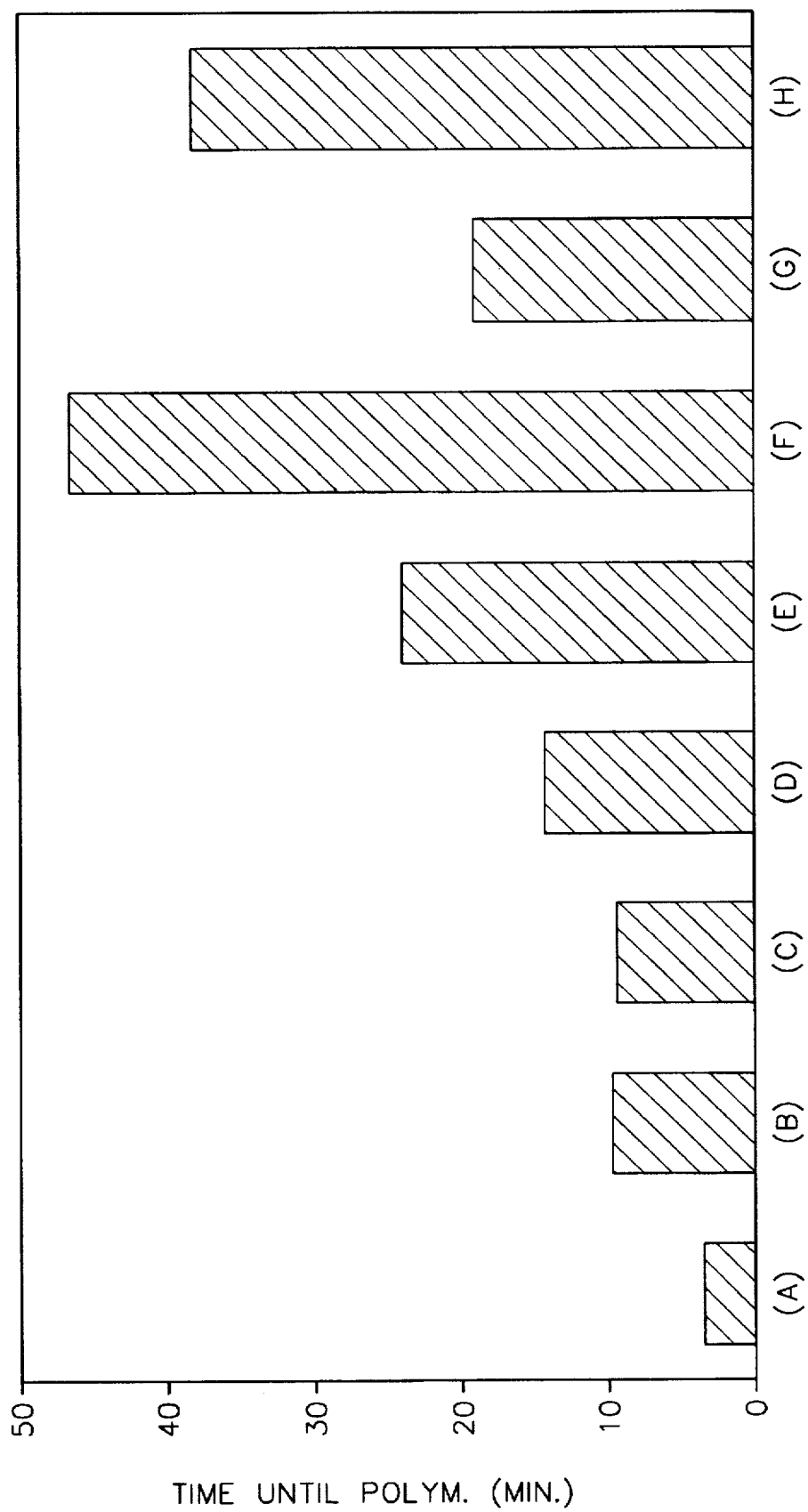
FIG. 1 is a bar graph representing some of the results of Example 2.
Figure 2A:
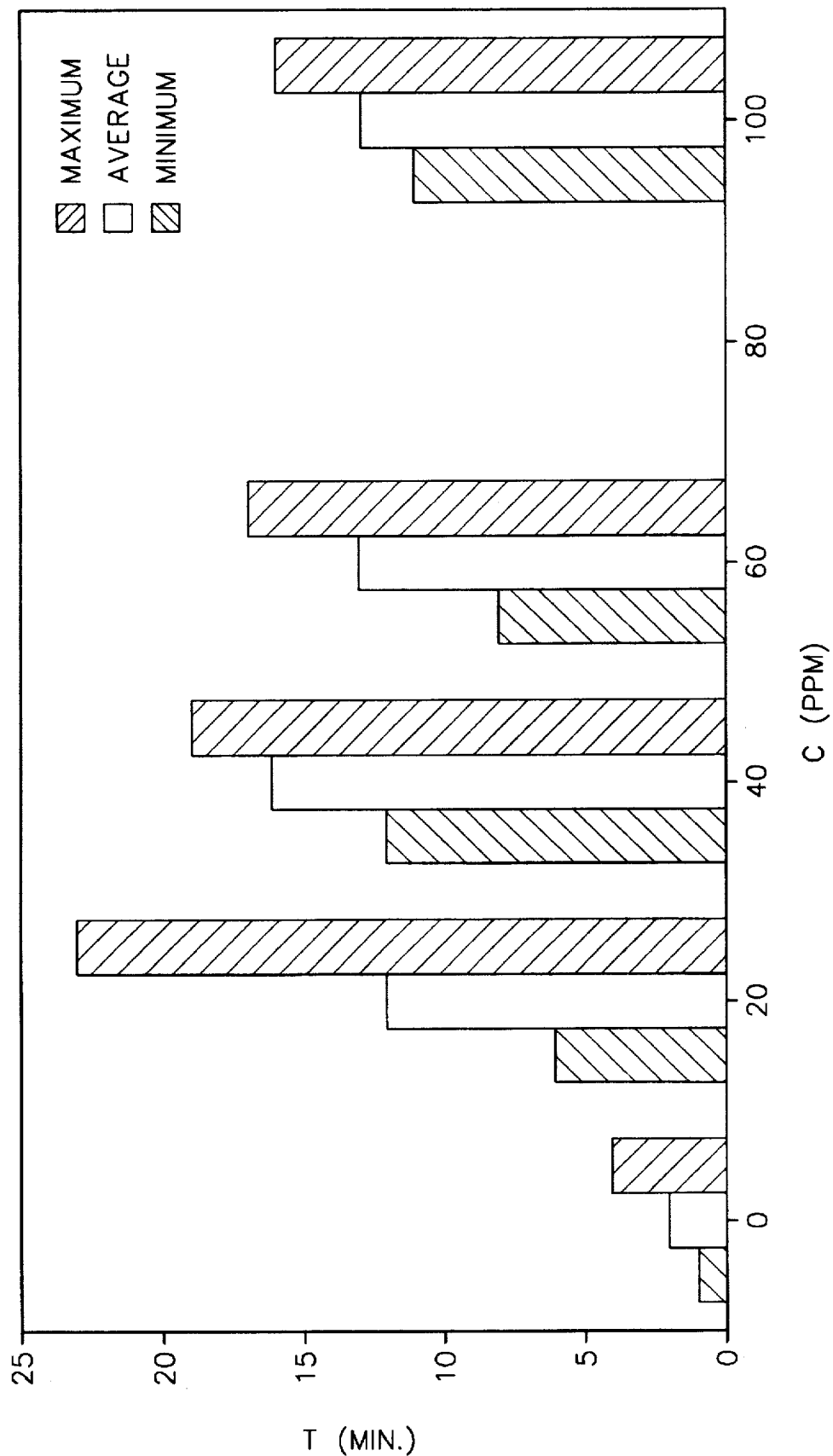
FIGS. 2A through 2D are bar graphs representing some of the results of Example 3.
Figure 2B:
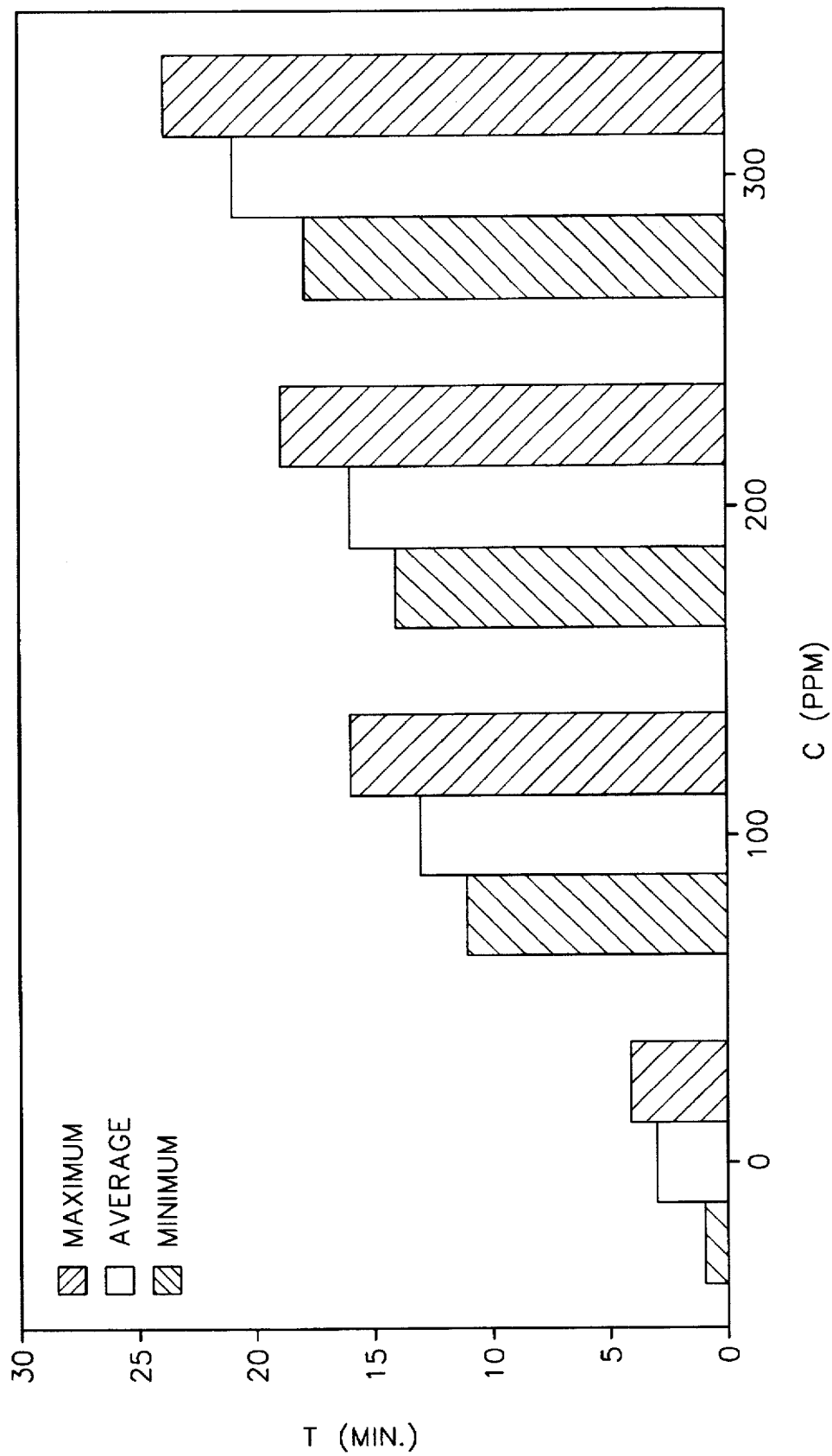
Figure 2C:
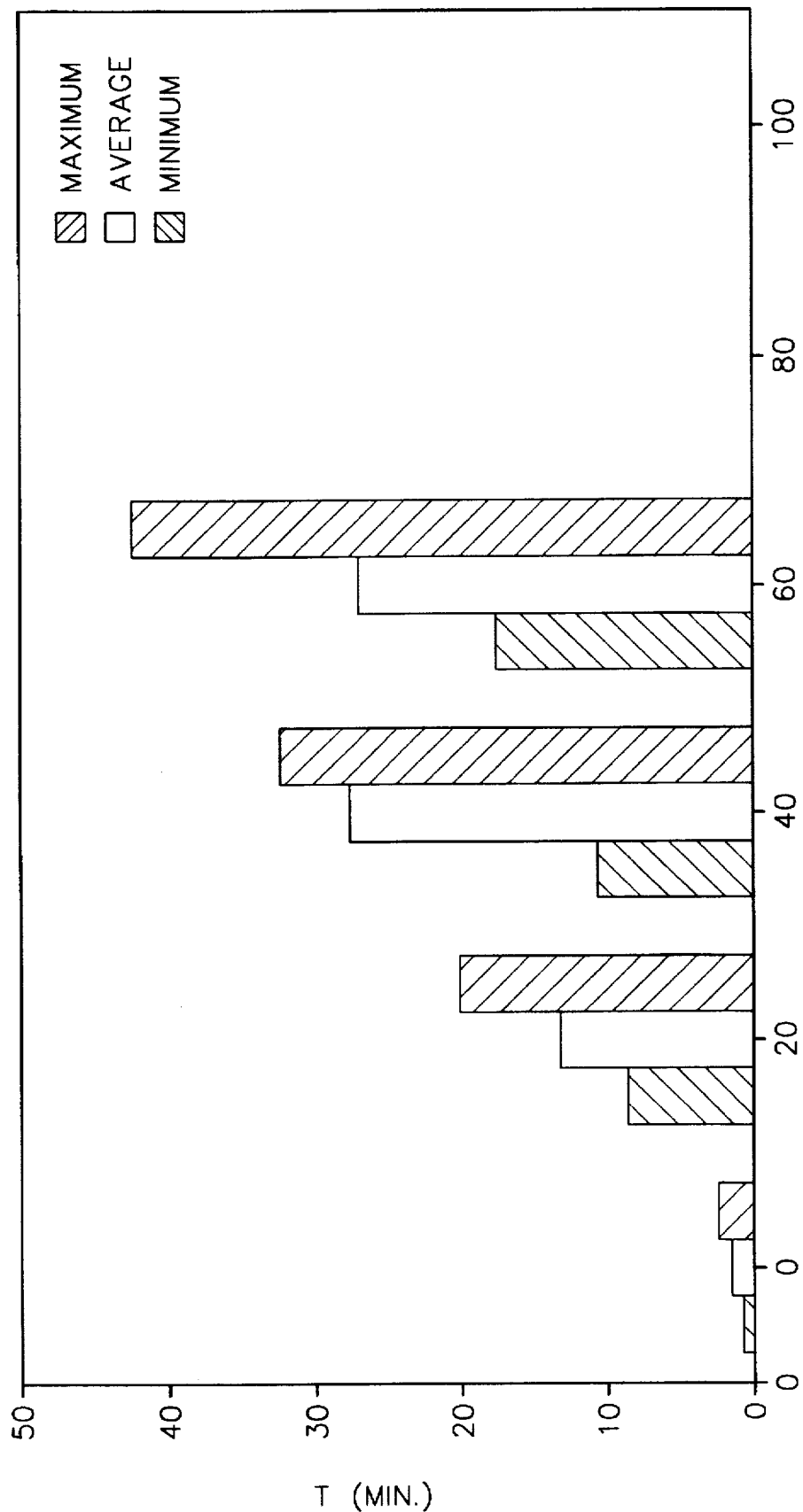
Figure 2D:
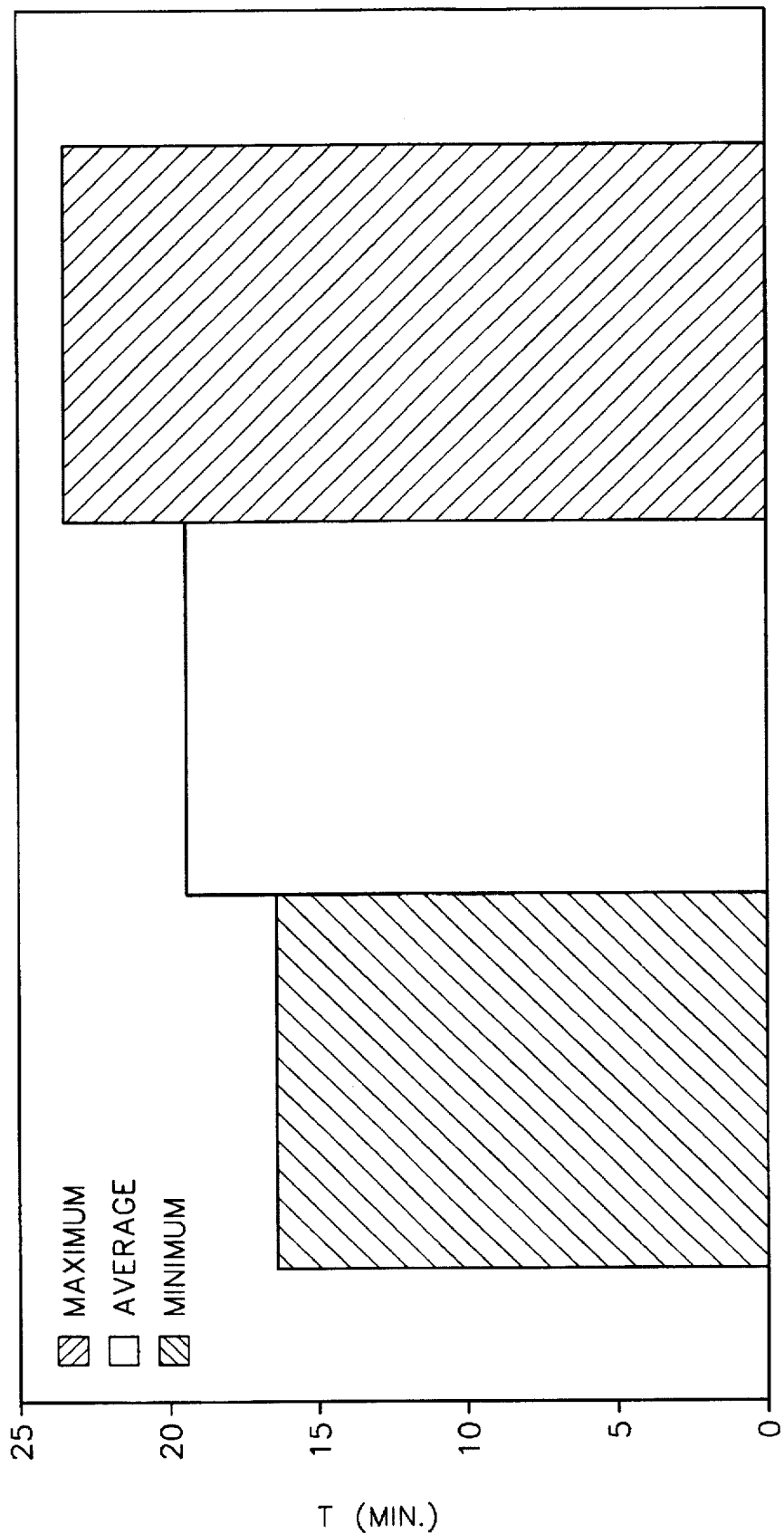

A stabilized acrylic acid composition is provided in which polymerization of the acrylic acid is inhibited during the distillation process for purifying or separating the acrylic acid as well as during transport and storage. The compositions of the present invention comprise: (A)acrylic acid, (B)a stable nitroxyl radical, e.g., HTEMPO, or its corresponding hydroxylamine and (C)a dihetero-substituted benzene compound having at least one transferable hydrogen, e.g., a quinone derivative such as MEHQ. During distillation, transport and storage, components (B) and (C) are present in a polymerization-inhibiting amount. During the distillation process, oxygen (D) is preferably added with components (B) and (C).

Suitable free radical for use in this invention is a stable nitroxyl radical (also called nitroxide) having the formula:

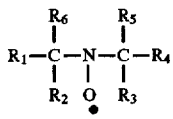

wherein $R_1$, $R_2$, $R_3$ and $R_4$ are alkyl groups or heteroatom substituted alkyl groups and no hydrogen is bound to the remaining valences on the carbon atoms bound to the nitrogen. Also suitable are the corresponding hydroxylamine thereof.

The alkyl (or heteroatom substituted) groups $R_1$–$R_4$ may be the same or different, and preferably contain 1 to 15 carbon atoms. Preferably $R_1$–$R_4$ are methyl, ethyl, or propyl groups. In addition to hydrogen the heteroatom substituents may include halogen, oxygen, sulfur, nitrogen and the like.

The remaining valences ($R_5$ and $R_6$) in the formula above may be satisfied by any atom or group except hydrogen which can bond covalently to carbon, although some groups may reduce the stabilizing power of the nitroxide structure and are undesirable. Preferably $R_5$ and $R_6$ are halogen, cyano, —$COOR_{11}$ wherein $R_{11}$ is alkyl or aryl, —$CONH_2$, —S—$C_6H_5$, —S—$COCH_3$, —$OCOC_2H_5$, carbonyl, alkenyl where the double bond is not conjugated with the nitroxide moiety, or alkyl of 1 to 15 carbon atoms. $R_5$ and $R_6$ may also form a ring structure with the nitrogen, preferably containing 4 or 5 carbon atoms and up to two heteroatoms, such as O, N or S. In such a situation, $R_5$ and $R_6$ may be designated by T and the nitroxide structure represented as follows:

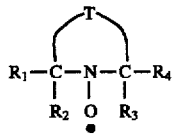

Further, two or more nitroxyl groups may be present in the same molecule, for example, by being linked through the T moiety by a linking group E as disclosed in U.S. Pat. No. 5,254,760, which is hereby incorporated by reference.

Examples of suitable compounds having the structure above and in which $R_5$ and $R_6$ form part of the ring are pyrrolidin-1-oxys, piperidinyl-1-oxys, the morpholines and piperazines. Particular examples wherein the $R_5$ and $R_6$ above form part of a ring are 4-hydroxy-2,2,6,6-tetramethyl-piperidino-1-oxy (HTEMPO); 2,2,6,6-tetramethyl-piperidino-1-oxy; 4-oxo-2,2,6,6-tetramethyl-piperidino-1-oxy; and pyrrolin-1-oxyl. Suitable $R_5$ and $R_6$ groups are methyl, ethyl, and propyl groups. A specific example of a suitable compound where $R_1$–$R_6$ are alkyl groups is di-tert-butylnitroxide. The preferred carbonyl containing nitroxides are those wherein the $R_5$ and $R_6$ form a ring structure with the nitrogen, preferably a six number ring, for example, 4-oxo-2,2,6,6-tetramethylpiperidino-1-oxy.

Examples of suitable nitroxide free radical compounds include, but re not limited to: di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethylpiperidinyloxy; 4-amino-2,2,6,6-tetramethylpiperidinyloxy; 4-ethanoyloxy-2,2,6,6-tetramethylpiperidinyloxy; 2,2,5,5-tetramethylpyrrolidinyloxy; 3-amino-2,2,5,5-tetramethylpyrrolindinyloxy; 2,2,5,5-tetramethyl-1-oxa-3-azacyclopentyl-3-oxy; 2,2,5,5-tetramethyl-3-pyrrolinyl-1-oxy-3-carboxylic acid; and 2,2,3,3,5,5,6,6-octamethyl-1,4-diazacyclohexyl-1,4-dioxy.

Examples of suitable hydroxylamines include, but are not limited to, the corresponding hydroxylamines of the nitroxides identified above.

Such stable nitroxide free radical compounds may be prepared by known methods, for example, see U.S. Pat. Nos. 3,494,930; 3,966,711; 3,704,233; 3,334,103; 3,253,055; 3,372,182; 3,502,692; 3,422,144; 3,163,677, 3,873,564 and 4,665,185, which are hereby incorporated by reference. The corresponding hydroxylamine may be prepared according to U.S. Pat. No. 4,665,185 and 5,290,888, which are hereby incorporated by reference. Such materials are also available from Aldrich Chemical Co. and Sigma Chemical Co.

Suitable dihetero-substituted benzene compounds having at least one transferable hydrogen are those having the formulae:

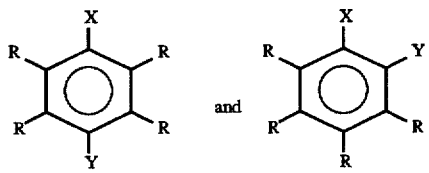

and combinations thereof, wherein X is OH or SH, and Y is $OR_7$, $NR_8R_9$ or $SR_{10}$, with X preferably being OH, R, $R_7$, $R_8$, $R_9$ and $R_{10}$ may be the same or different, and preferably contain 1 to 15 carbon atoms with R also preferably being H (hydrogen). Preferably, $R_7$, $R_8$, $R_9$ and $R_{10}$ are methyl, ethyl, propyl, butyl, or phenyl and the R groups H. The alkyl groups may also contain heteroatom substituents, such as halogen, oxygen, sulfur, nitrogen, and the like.

Examples of such dihetero-substituted benzene compounds include, but are not limited to: hydroquinone; 4-methoxyphenol; 4-ethoxyphenol; 4-propoxyphenol and propyl isomers thereof; 4-butoxyphenol and butyl isomers thereof; 4-heptoxyphenol and heptyl isomers thereof; hydroquinone, monobenzylether; 1,2-dihydroxybenzene; 2-methoxyphenol; 2,5-dichlorohydroquinone; 2,5-di-tert-butylhydroquinone; 2-acetylhydroquinone; hydroquinone, monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol;

4-mercaptophenol; catechol; monobutylether and butyl isomers thereof; 4-ethylaminophenol; 2,3-dihydroxyacetophenone; pyrogallol, 1,2-dimethylether; and 2-methylthiophenol. Such compounds are well known and commercially available.

Preferably, component (B) is present in an amount of from about 5.8 millimolar to about 5.8 molar parts per million of acrylic acid on a weight basis (ppm), and component (C) is present in an amount of from about 8 millimolar to about 16 molar ppm. During distillation, component amount of preferably present in an amount of from about 1 to about 15,000 ppm, with the ppm being based on oxygen content. Component (D) may be added as air or molecular oxygen.

More preferably, component (B) is present in an amount of from about 5.8 millimolar to about 3.5 molar ppm, and component (C) is present in an amount of from about 8 millimolar to about 9.7 molar ppm. If present during distillation, component (D) is more preferably present in an amount of from about 5 to about 5,000 ppm. Most preferably, component (B) is present in an amount of from about 5.8 millimolar to about 1.7 molar ppm, and component (C) is present in an amount of from about 8 millimolar to about 9.7 molar ppm. During distillation, component (D) is most preferably present in an amount of from about 5 to about 1,000 ppm.

In one particularly preferred embodiment, components (B) and (C) are present in a molar ratio of from about 1:9 to about 9:1.

In another particularly preferred embodiment, components (B) and (C) are present in a molar ratio of from about 1:3 to about 3:1.

In another particularly preferred embodiment, components (B) and (C) are present in a molar ratio of from about 2:3 to about 3:2.

The oxygen may be present or added as molecular oxygen or as air. Air is preferred. The oxygen, whether molecular or present in air, may be added at any point within the distillation column but is preferably added at the bottom of the distillation column.

The amounts in which the components (B) and (C) and, if present, the oxygen (D) are used will vary depending upon various conditions including the distillation, operating conditions and storage and transport conditions.

The foregoing components (B) and (C) dissolve with relative ease in acrylic acid or organic solvents that are used in the process of preparing acrylic acid. During distillation, the oxygen is typically introduced into the distillation column in the gaseous state.

The composition which includes component (D) may be used in the various distillation steps that are carried out in the distillation column for purifying acrylic acid, for separating acrylic acid from the solvent, for separating such light fractions as acetic acid from acrylic acid, for separating acrylic acid from acrylic esters and alcohol, and for separating such light fraction as acrolein from the aqueous solution of acrylic acid.

The composition is also useful in the various steps that are carried out in the condensation column for acrylic acid and in the esterification reactor.

The compositions of the invention may be stored, handled, and used as monomeric material in polymerization processes, and otherwise, with continuing inhibition of thermal polymerization.

The present invention is further illustrated by the following non-limiting examples. All parts, percentages and other amounts given throughout this disclosure are by weight unless otherwise indicated.

EXAMPLES

EXAMPLE 1

NITROXIDE SYNTHESIS

In this example, the nitroxide HTEMPO was prepared according to the method disclosed in Sosnovsky and Konieczny, Z. Naturforsch, Vol. 31b, pp. 1376–78 (1976), for use in the polymerization inhibition tests which follow. About 9.43 grams of 2,2,6,6-tetramethyl-4-piperidinol was dissolved in about 80 ml. of water. About 1 ml. of Versenex 80 was added to the mixture. Thereafter, about 27.2 ml. of hydrogen peroxide (30%) was also added. About 0.4 grams of sodium tungstate ($Na_2WO_4$—$2H_2O$) were then added thereto. The total water volume is about 99 ml. The reaction solution was stirred vigorously at room temperature overnight. Thereafter, about 23.73 grams of sodium carbonate (anhydrous) were dissolved and the reaction solution was stirred. A deep red product separated and became the upper phase. On standing, this upper phase crystallized giving the crude nitroxide. The nitroxide was then filtered, then redissolved in ether. Inorganic salts were removed by filtration. The solvent was evaporated to give crude nitroxide. The nitroxide was then purified by crystallizing from cyclohexane. A yield of 8.95 grams (about 83.3%) recrystallized. The aqueous filtrate may be further extracted to remove residual nitroxide. The piperidinol has a molecular weight of 157.26 and a melting point of 131° C. The nitroxide had a molecular weight of 172.26 and a melting point of about 70° C. The extraction of the nitroxide may also be performed with a xylene/butyl cellosolve (e.g., using a weight ratio of 49/2).

EXAMPLE 2

STABILIZATION OF ACRYLIC ACID

In this experiment, acrylic acid was stabilized with HTEMPO alone, MEHQ alone and the combination of HTEMPO and MEHQ. The HTEMPO was that prepared in Example 1. The remaining materials utilized were lab grade chemicals obtained from Aldrich or Sigma. These included acrylic acid (AA), hydroquinone (HQ), monoomethylether of hydroquinone (MEHQ), mono-ethyl-ether of hydroquinone (EEHQ), mono-heptyl-ether of hydroquinone (C7HQ), phenothiazine (PTZ), butylated hydroxy toluene (BHT) and N,N'-di-sec-butylphenylenediamine (PDA).

The experiments were carried out using a DuPont Instruments 9000 Thermal Analyzer with a DSC 10 Differential Scanning Calorimeter with pressure unit. The Differential Scanning Calorimeter was supplied by TA (formerly STA) of Alzenau, Germany.

The acrylic acid utilized herein had previously been stabilized with MEHQ. The monomer was purified by removal of the inhibitor through careful distillation under an oil pump vacuum. The purified monomer was collected at −70° C. and aliquots of it were stored in a freezer at about −30° C. The absence of MEHQ was confirmed through high pressure chromatography (HPLC), gas chromatography (GC) and gc-mass-spectrometry (GCMS).

The potential influence of different inhibitors to stabilize acrylic acid against unwanted, thermally initiated, radical polymerization was determined using differential scanning calorimetry (DSC). A sample (usually 2 to 4 μl) of the monomer with or without the inhibitor was encapsulated in a small aluminum sample container. An empty one was used as a reference. Because the thermally induced radical polymerization of AA is exothermic by nature, the difference of the generated thermal energy between the sample and the blank was measured by the DSC and registered as a positive peak in the printout.

All experiments described herein were run using the same conditions, e.g., sample preparation, thermal condition (about 136° C.), determining the onset of polymerization (from DSC printout), etc. It was demonstrated that, for example, a change in the heat-up rate to the desired temperature of about 136° C. had no significant influence on the induction time (i.e., time until polymerization could be observed). Other variations, e.g., decrease of the maximum temperature, resulted in the expected change of the induction time (i.e., longer time).

Although MEHQ and HTEMPO may be used as stabilizers for acrylic acid alone, their individual stabilization effect was significantly less than their combination. The combination of the two had a synergistic effect on the stabilization of AA. Specifically, the effect was significantly greater than the added effect of the individual components. The improvement became visible when the amount of one added to the other was at least about 10% of the total amount of inhibitor.

It was found that the described synergy seemed to depend on the presence of both the hydroquinone derivative and the nitroxide. The effect was best with MEHQ but could also be observed with EEHQ and C7-HQ. This could be explained by the fact that the dosage was weight ppm and, therefore, a greater molecular weight (of EEHQ and C7-HQ compared to MEHQ) resulted in less inhibitor in the samples measured (i.e., not mole corrected). No difference was observed between lab and technical grade acrylic acid.

FIG. 1 shows the results as retention time of the most important experiments:

| | |
|---|---|
| (A) | purified AA. |
| (B + C)cal. | the theoretical, calculated, result if the effect would only be additive for MEHQ (200 ppm) with HTEMPO (100 ppm). |
| (B + C')cal | the theoretical, calculated result if the effect would only be additive for EEHQ (200 ppm) with HTEMPO (100 ppm). |
| (B + C)act. | the result of a combination of 200 ppm of MEHQ with 100 ppm of HTEMPO. |
| (B + C')act. | the result of a combination of 200 ppm if EEHQ with 100 ppm HTEMPO. |

EXAMPLE 3

STABILIZATION OF METHACRYLIC ACID (COMPARATIVE EXAMPLE)

In this experiment, methacrylic acid was stabilized with HTEMPO alone, MEHQ alone and a combination thereof with each variation performed 5 or 6 times. The materials for the experiments described herein came from the same sources as mentioned in Example 2, this includes methacrylic acid, MAA.

Methacrylic acid was purified using the same technique as with AA in Example 2. The absence of the inhibitor (MEHQ) was again confirmed by GCMS.

DSC was used to measure the influence of the different inhibitors on the thermally induced radical polymerization of methacrylic acid. Sample containers and sample volumes were identical to that of AA in Example 2.

The only difference between the work carried out with AA and MAA was the temperature used to initiate polymerization. In order to make it easier to compare AA with MAA, MAA was run at the same temperature as AA (136° C.–137° C.), but variations in the results coming from that relatively low temperature increased the scatter in the results making them non-reproducible. Therefore, 159° C. was chosen, which is close to the boiling point of MAA, but even here scattering exists and is relatively greater than with AA.

In comparing the two different radicals

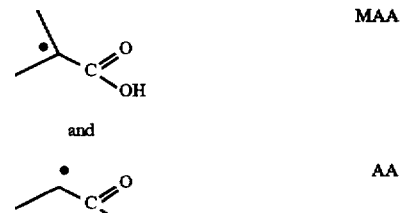

it becomes apparent that the MAA free radical is the more stable species (stabilized through the —$CH_3$ group). Tertiary radicals such as these are made more stable (i.e., less reactive) than secondary radicals, e.g., MAA vs. AA radicals. Accordingly, the MAA radical is less reactive than the AA radical.

This is reflected in the results of the experiments described here. Only very small amounts of inhibitor were necessary to stabilize MAA, the biggest effect (in %) was between the purified monomer and 20 ppm of both HTEMPO or MEHQ.

A combination of HTEMPO and MEHQ (20 and 30 ppm, respectively, for a 50 ppm total) did not show a better inhibition than the sum of the effects of the individual inhibitors alone, each at 50 ppm. This suggested that in the MAA system the synergy observed in AA does not exist. See FIGS. 2A–2D.

EXAMPLE 4

STABILIZATION OF ACRYLIC ACID WITH HTEMPO AND MEHQ VARYING THE RELATIVE CONCENTRATION OF EACH

In this experiment, acrylic acid was stabilized with HTEMPO alone, MEHQ alone, and a combination thereof while maintaining the total concentration thereof at 300 ppm. The test procedure and set-up were like that of Example 2.

TABLE 1

| | Concentration (ppm) | | |
|---|---|---|---|
| Run No. | HTEMPO | MEHQ | Time (min.)* |
| 1 | 0 | 0 | 4.1 |
| 2 | 0 | 300 | 22.1 |
| 3 | 75 | 225 | 36.2 |
| 4 | 100 | 200 | 44 |
| 5 | 125 | 175 | 40.9 |
| 6 | 150 | 150 | 36.1 |
| 7 | 200 | 100 | 29.1 |
| 8 | 300 | 0 | 12.2 |

*Time until polymerization.

The synergistic effect of the combination of HTEMPO and MEHQ is readily apparent from Table 1 in that the time until polymerization starts is delayed significantly.

EXAMPLE 5

STABILIZATION OF ACRYLIC ACID

In this experiment, acrylic acid was stabilized with MEHQ alone, HTEMPO alone, and a combination of MEHQ and HTEMPO, and a combination of MEHQ and the corresponding hydroxylamine of HTEMPO. The test procedure and set-up was like that of Example 2.

TABLE 2

| Run No. | Concentration (ppm) | | | Time (Min.)* |
| | MEHQ | HTEMPO | HYDROXYLAMINE | |
| --- | --- | --- | --- | --- |
| 1 | 0 | 0 | 0 | 4.1 |
| 2 | 300 | 0 | 0 | 22.1 |
| 8 | 0 | 300 | 0 | 12.2 |
| 4 | 200 | 100 | 0 | 44 |
| 9 | 200 | 0 | 100 | 33.4 |

*Time until polymerization.

As is readily apparent from Table 2, there is also a synergistic effect when a combination of MEHQ and the corresponding hydroxylamine of HTEMPO is utilized.

EXAMPLE 6

STABILIZATION OF ACRYLIC ACID

In experiments acrylic acid was stabilized with a combination of HTEMPO and MEHQ. Additional stabilizations were performed by replacing a position of the HTEMPO with HQ. MEHQ dose was maintained at 200 ppm with the HTEMPO/HQ variable totaling 100 ppm. Otherwise, the test procedure and set-up were like that of Example 2.

TABLE 3

| Run No. | Concentration (ppm) | | | Time (Min.)* |
| | MEHQ | HQ | HTEMPO | |
| --- | --- | --- | --- | --- |
| 10 | 200 | 80 | 20 | 84.9 |
| 11 | 200 | 50 | 50 | 84.8 |
| 12 | 200 | 20 | 80 | 73.4 |
| 13 | 200 | 0 | 100 | 58.8 |

*Time until polymerization.

As is readily apparent from Table 3, there is also a synergistic effect when a combination of MEHQ, HQ and HTEMPO is utilized.

It is understood that the foregoing detailed description is given by way of illustration and that many modifications may be made therein without departing from the spirit or scope of the present invention.

What is claimed is:

1. A monomer composition, stabilized against premature polymerization, said composition comprising a mixture of (a) acrylic acid; and (b) an effective amount, sufficient to inhibit premature polymerization of the acrylic acid, of a combination of
        (i) a compound selected form the group consisting of a stable nitroxyl radical, its corresponding hydroxylamine and combinations thereof, and
        (ii) a dihetero-substituted benzene compound having at least one transferable hydrogen.

2. The composition of claim 1, wherein the compound is a stable nitroxyl radical having the formula:

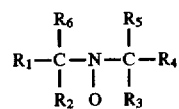

wherein $R_1$, $R_2$, $R_3$ and $R_4$ each are alkyl groups or heteroatom substituted alkyl groups and $R_5$ and $R_6$ each are halogen, cyano, —$COOR_{11}$ wherein $R_{11}$ is alkyl or aryl, —$CONH_2$, —S—$C_6H_5$, —S—$COCH_3$, —$OCOC_2H_5$, carbonyl, alkenyl where the double bond is not conjugated with the nitroxyl moiety, or alkyl of 1 to 15 carbon atoms or $R_5$ and $R_6$ together form a ring structure with the nitrogen of the nitroxyl moiety.

3. The composition of claim 2, the stable nitroxyl radical is selected from the group consisting of: di-tert-butylnitroxide; di-tert-amylnitroxide; 2,2,6,6-tetramethyl-piperidinyloxy; 4-hydroxy-2,2,6,6-tetramethyl-piperidinyloxy (HTEMPO); 4-oxo-2,2,6,6-tetramethyl-piperidinyloxy; 4-dimethylamino-2,2,6,6-tetramethylpiperidinyloxy; 4-amino-2,2,6,6-tetramethylpiperidinyloxy; 4-ethanoyloxy-2,2,6,6-tetramethylpiperidinyloxy; 2,2,5,5-tetramethylpyrrolidinyloxy; 3-amino-2,2,5,5-tetramethylpyrrolindinyloxy;2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; and combinations thereof.

4. The composition of claim 3, the stable nitroxyl radical is 4-hydroxy-2,2,6,6-tetramethyl-piperidinyloxy (HTEMPO).

5. The composition of claim 1, wherein the dihetero-substituted benzene compound having at least one transferable hydrogen is selected from the group consisting of those having the formulae:

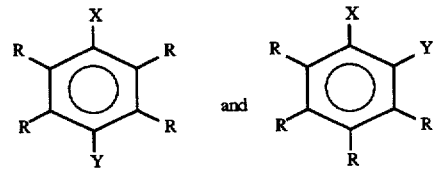

and combinations thereof, wherein X is OH or SH, and Y is $OR_7$, $NR_8R_9$ or $SR_{10}$, wherein $R_7$ and $R_{10}$ are each hydrogen, $C_1$–$C_5$ alkyl or aryl, $R_8$ and $R_9$ are each $C_1$–$C_{15}$ alkyl or aryl, and R is hydrogen or $C_1$–$C_{15}$ alkyl.

6. The composition of claim 1, wherein the dihetero-substituted benzene compound having at least one transferable hydrogen is selected from the group consisting of: hydroquinone; 4-methoxyphenol (MEHQ); 4-ethoxyphenol; 4-propoxyphenol and propyl isomers thereof; 4-butoxyphenol and butyl isomers thereof; 4-heptoxyphenol and heptyl isomers thereof; hydroquinone, monobenzylether; 1,2-dihydroxybenzene; 2-methoxyphenol; 2,5-dichlorohydroquinone; 2,5-di-tert-butylhydroquinone; 2-acetylhydroquinone; hydroquinone, monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol; 4-mercaptophenol; catechol; monobutylether and butyl isomers thereof; 4-ethylaminophenol; 2,3-dihydroxyacetophenone; pyrogallol, 1,2-dimethylether; 2-methylthiophenol; and combinations thereof; provided that hydroquinone is used in combination with at least one other dihetero-substituted benzene compound having at least one transferable hydrogen.

7. A process for preventing the premature polymerization of acrylic acid, said process comprising adding to said acrylic acid an effective amount, sufficient to inhibit premature polymerization of said acrylic acid, of a combination of
(a) a compound selected form the group consisting of a stable nitroxyl radical, its corresponding hydroxylamine and combinations thereof, and
(b) a dihetero-substituted benzene compound having at least one transferable hydrogen.

8. The process of claim 7, wherein the compound is a stable nitroxyl radical having the formula:

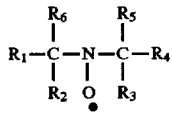

wherein $R_1$, $R_2$, $R_3$ and $R_4$ each are alkyl groups or heteroatom substituted alkyl groups and $R_5$ and $R_6$ each are halogen, cyano, —$COOR_{11}$ wherein $R_{11}$ is alkyl or aryl, —$CONH_2$, —S—$C_6H_5$, —S—$COCH_3$, —$OCOC_2H_5$, carbonyl, alkenyl where the double bond is not conjugated with the nitroxyl moiety, or alkyl of 1 to 15 carbon atoms or $R_5$ and $R_6$ together form a ring structure with the nitrogen of the nitroxyl moiety.

9. The process of claim 8, the stable nitroxyl radical is selected from the group consisting of: di-tert-butylnitroxide; di-tert-amylnitroxide; 2,2,6,6-tetramethyl-piperidinyloxy; 4-hydroxy-2,2,6,6-tetramethyl-piperidinyloxy (HTEMPO); 4-oxo-2,2,6,6-tetramethyl-piperidinyloxy; 4-dimethylamino-2,2,6,6-tetramethylpiperidinyloxy; 4-amino-2,2,6,6-tetramethylpiperidinyloxy; 4-ethanoyloxy-2,2,6,6-tetramethylpiperidinyloxy; 2,2,5,5-tetramethylpyrrolidinyloxy; 3-amino-2,2,5,5-tetramethylpyrrolindinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; and combinations thereof.

10. The process of claim 9, the stable nitroxyl radical is 4-hydroxy-2,2,6,6-tetramethyl-piperidinyloxy (HTEMPO).

11. The process of claim 7, wherein the dihetero-substituted benzene compound having at least one transferable hydrogen is selected from the group consisting of those having the formulae:

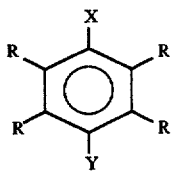 and 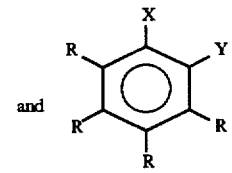

and combinations thereof, wherein X is OH or SH, and Y is $OR_7$, $NR_8R_9$ or $SR_{10}$, wherein $R_7$ and $R_{10}$ are each hydrogen, $C_1$–$C_{15}$ alkyl or aryl, $R_8$ and $R_9$ are each $C_1$–$C_{15}$ alkyl or aryl, and R is hydrogen or $C_1$–$C_{15}$ alkyl.

12. The process of claim 7, wherein the dihetero-substituted benzene compound having at least one transferable hydrogen is selected from the group consisting of: hydroquinone; 4-methoxyphenol (MEHQ); 4-ethoxyphenol; 4-propoxyphenol and propyl isomers thereof; 4-butoxyphenol and butyl isomers thereof; 4-heptoxyphenol and heptyl isomers thereof; hydroquinone, monobenzylether; 1,2-dihydroxybenzene; 2-methoxyphenol; 2,5-dichlorohydroquinone; 2,5-di-tert-butylhydroquinone; 2-acetylhydroquinone; hydroquinone, monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol; 4-mercaptophenol; catechol; monobutylether and butyl isomers thereof; 4-ethylaminophenol; 2,3-dihydroxyacetophenone; pyrogallol, 1,2-dimethylether; 2-methylthiophenol; and combinations thereof; provided that hydroquinone is used in combination with at least one other dihetero-substituted benzene compound having at least one transferable hydrogen.

* * * * *